United States Patent [19]

Anantaraman

[11] Patent Number: 4,583,395
[45] Date of Patent: Apr. 22, 1986

[54] VISCOMETER

[75] Inventor: Ayilam V. Anantaraman, Nepean, Canada

[73] Assignee: Her Majesty the Queen in right of Canada, as represented by the Minister of National Defence, Ottawa, Canada

[21] Appl. No.: 737,844

[22] Filed: May 24, 1985

[51] Int. Cl.⁴ .......................................... G01N 11/06
[52] U.S. Cl. ...................................................... 73/55
[58] Field of Search .......................................... 73/55

[56] References Cited

U.S. PATENT DOCUMENTS

| 2,048,305 | 7/1936 | Ubbelohde | 73/55 |
|---|---|---|---|
| 2,091,896 | 8/1937 | Ubbelohde | 73/55 |
| 2,095,282 | 10/1937 | Payne | 73/55 |
| 2,343,061 | 2/1944 | Irany | 73/55 |
| 2,805,570 | 9/1957 | Cannon | 73/55 |
| 3,277,694 | 10/1966 | Cannon et al. | 73/55 |
| 3,559,463 | 2/1971 | Tovrog et al. | 73/55 |
| 3,699,804 | 10/1972 | Gassmann et al. | 73/55 |
| 3,981,182 | 9/1976 | Kössler et al. | 73/55 |
| 4,028,929 | 6/1977 | Bohm | 73/55 |

FOREIGN PATENT DOCUMENTS

| 1032576 | 6/1958 | Fed. Rep. of Germany | 73/55 |
|---|---|---|---|
| 2442943 | 4/1975 | Fed. Rep. of Germany | 73/55 |
| 2950010 | 6/1981 | Fed. Rep. of Germany | 73/55 |
| 3014705 | 10/1981 | Fed. Rep. of Germany | 73/55 |
| 2373050 | 8/1978 | France | 73/55 |
| 271092 | 8/1970 | U.S.S.R. | 73/55 |

OTHER PUBLICATIONS

Holcomb, L. A., *Calibration of Kinematic Viscometers*, In Instr. and Control Sys., vol. 37, pp. 109–115, Feb. 1964.

Primary Examiner—Stewart J. Levy
Assistant Examiner—Joseph W. Roskos
Attorney, Agent, or Firm—Anthony T. Lane; Robert P. Gibson; Michael C. Sachs

[57] ABSTRACT

A viscometer for measuring the viscosity of volatile liquids or liquids that are easily contaminated in the air, is disclosed. The viscometer is of the capillary type and includes a U-shaped tube with a capillary adjacent the bight in one arm and a collector adjacent the bight in the other arm. In addition, the arm containing the capillary has two bulbs in series above the capillary and a stopcock adjacent the upper end. The other arm is equipped with a reservoir for a liquid sample to be tested, a branch passage adjacent the top and a plug valve for closing off the arm below the branch passage. The two arms are joined by a bypass above the reservoir and the bulbs. A stopcock is included in the bypass.

5 Claims, 1 Drawing Figure

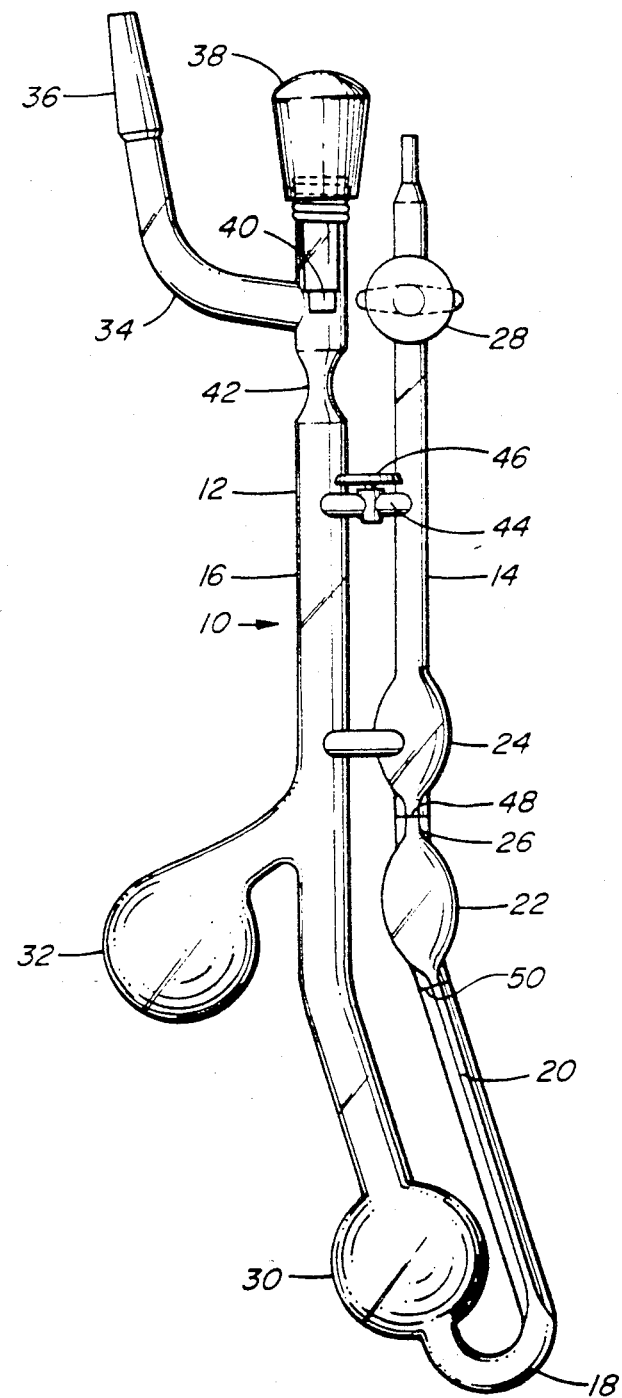

VISCOMETER

The present invention relates to viscometers and more particularly to viscometers for measuring the viscosity of volatile liquid or liquids that are easily contaminated in the air.

Methods of measuring viscosities of volatile and hygroscopic liquids are not properly described in the literature. Ball type viscometers do not provide the required accuracy, and are not suitable for such systems. Capillary viscometers, based on the Ostwald type have been used for measurement on such mixtures, but the data is unreliable and of questionable validity. The major limitations of existing capillary type viscometers when dealing with volatile and readily contaminated liquids are:

(a) The apparatus is an open system, leading to the contamination of the test sample.

(b) A considerable loss of solvent and solute is possible, particularly where these are volatile.

(c) It is difficult to introduce highly volatile solute and gases.

The present invention proposes an apparatus designed for kinematic viscosity measurements of liquid systems involving very hygroscopic solvents and volatile solutes such as a gas.

According to the present invention there is provided a viscometer comprising a substantially U-shaped tube having a bight and a first and second arm, a capillary in the first arm adjacent the bight, a stopper for each arm remote from the bight, a branch passage joining the first arm between the stopper and the capillary to the second arm between the stopper and the bight, and a valve in the branch passage.

The apparatus is a modification of the known Cannon-Fenske type capillary viscometer. However, the viscometer may be completely closed against the atmosphere when in use so as to prevent contamination or the loss of volatile components.

Preferably, the apparatus includes a reservoir for liquid that is branched off the second arm between the stopper and the bight. A liquid can be introduced to the reservoir and then frozen while the viscometer is subjected to a vacuum to remove contaminants from the viscometer. The reservoir is also useful for degassing the liquid by repeated freezing and thawing.

A collector may be employed in the second arm between the stopper and the bight. This is in the form of a bulb-type enlargement in the arm.

In most preferred embodiments, the first arm includes two bulbs, one directly above the capillary and the other spaced slightly above the first bulb. Two marks may then be provided on the first tube on opposite sides of the first bulb. In use of the viscometer, the time for flow between the two marks is taken as in measure of the viscositiy.

To facilitate the introduction of liquids, the second arm is preferably provided with a branch passage and a stopper in the form of a plug valve for closing the second arm below the branch passage.

The accompanying drawing illustrates an exemplary embodiment of the present invention.

Referring to the drawing, there is illustrated a viscometer 10, the main component of which is a glass tube 12 formed into a generally U-shape with a first arm 14, a second arm 16 and a bight 18 joining the two arms. The first arm 14 has a capillary section 20 leading from the bight 18. The capillary leads into a bulb 22 which, in turn, leads to a second bulb 24 through a neck 26 in the tube. Adjacent its upper end, the first arm 14 is equipped with a stopcock 28.

The second arm 16 has an enlarged collector 30 adjacent the bight and a pear-shaped reservoir 32 branching off the arm 16 above the collector. At its upper end, the second arm 16 has a branch passage 34 ending in a ground glass joint 36. A rotary stopper 38 in the form of a plug valve is fitted to the end of the arm 16. When the stopper 38 is closed, its plug 40 engages a seat 42 in the arm 16 to close off the arm 16 below the branch passage 34. The two arms 12 and 14 are bridged by a branch passage 44 leading from a position on the first arm 14 between the stopcock 28 and the second bulb 24 to a position on the second arm 16 between the valve seat 42 and the reservoir 32. The branch passage 44 is equipped with a stopcock 46.

To use the described viscometer, a gas tight syringe is connected to the outlet of the stopcock 28 by a short piece of silicon rubber tubing. The stopcocks 28 and 46 are slightly greased and the clean, dry viscometer assembly is weighed.

With the stopcocks 28 and 46 and the stopper 38 open, the instrument is placed in an argon glove box. The required volume of high purity liquid test sample is introduced into the pear shaped reservoir 32 through the branch passage 34 of the second arm 16. The stopcocks 28 and 46 and the rotary stopper 38 are closed and the unit is removed from the glove box. A vacuum line is then connected to the ground glass joint 36 and the liquid is frozen, for example by submerging the reservoir in liquid nitrogen. Opening the rotary stopper 38 allows the vacuum to draw off any gases in the viscometer. If desired, the solvent may be degassed by closing the rotary stopper 38, thawing and subsequently freezing the sample and reopening the rotary stopper 38 to draw off any gases. The procedure may be repeated a number of times if necessary.

After any necessary degassing has been completed, the rotary stopper 38 is closed and the viscometer is removed from the vacuum line. The sample in the reservoir 32 is melted and poured from the reservoir 32 into the collector 30 and the bight 18 of the tube tube 12. The viscometer is then set in a thermostaticly controlled bath with the capillary tube 20 in a vertical orientation. The vertical orientation is not critical, but it is ideal. The orientation should, in any event, remain the same for all test runs with the viscometer.

Once the viscometer has attained temperature equilibrium, the stopcock 28 is opened and the syringe is used to draw the liquid sample from the collector 32 up the arm 14 past a mark 48 on the neck 26 between the bulbs 22 and 24. The stopcock 46 is then opened and the vapour drawn into the syringe is slowly pushed back into the viscometer with the syringe. The stopcock 28 is then closed and the time for flow between the mark 48 and a mark 50 on the tube immediately below the bulb 22 is taken as a measure of viscosity. The procedure can be repeated for consistency. If a volatile component, such as a gas, is to be added to the liquid sample, the viscometer is weighed in order to determine the initial weight of liquid. The liquid in the viscometer is transferred into the reservoir 32 by slowly tilting the viscometer. The liquid is then frozen. The stopcocks S1 and S2 remain closed and the rotary stopper 38 is opened to admit the solute gas. The rotary stopper 38 is then closed. The amount of gas transferred can be determined from the weight of the assembly. The viscosity of the solution can then be determined as described above. The procedure can be continued for further incremental additions of solute gas.

The embodiments of the invention in which an exclusive property or privilege is claimed are defined as follows:

1. A viscometer comprising a substantially U-shaped tube having a bight and a first and second arms, a capillary in the first arm adjacent the bight, a stopper for each arm remote from the bight, a branch passage joining the first arm between the stopper and the capillary to the second arm between the stopper and the bight, a valve in the branch passage, a reservoir for liquid branched off the second arm between the stopper and the bight, and a collector in the second arm between the reservoir and the bight.

2. A viscometer comprising a substantially U-shaped tube having a bight and a first and second arms, a capillary in the first arm adjacent the bight, a stopper for each arm remote from the bight, a branch passage joining the first arm between the stopper and the capillary to the second arm between the stopper and the bight, a valve in the branch passage, a reservoir for liquid branched off the second arm between the stopper and the bight, a collector in the second arm between the reservoir and the bight, and a first bulb in the first arm above and adjacent the said capillary.

3. A viscometer comprising a substantially U-shaped tube having a bight and a first and second arms, a capillary in the first arm adjacent the bight, a stopper for each arm remote from the bight, a branch passage joining the first arm between the stopper and the capillary to the second arm between the stopper and the bight, a valve in the branch passage, a reservoir for liquid branched off the second arm between the stopper and the bight, a collector in the second arm between the reservoir and the bight, a first bulb in the first arm above and adjacent the capillary, and a second bulb in the first arm above the first bulb.

4. A viscometer comprising a substantially U-shaped tube having a bight and a first and second arms, a capillary in the first arm adjacent the bight, a stopper for each arm remote from the bight, a branch passage joining the first arm between the stopper and the capillary to the second arm between the stopper and the bight, a valve in the branch passage, a reservoir for liquid branched off the second arm between the stopper and the bight, a collector in the second arm between the reservoir and the bight, a first bulb in the first arm above and adjacent the capillary, and a second bulb in the first arm above the first bulb, said viscometer further including two marks, on the first arm, adjacent and on opposite sides of the first bulb.

5. A viscometer comprising a substantially U-shaped tube having a bight and a first and second arms, a capillary in the first arm adjacent the bight, a stopper for each arm remote from the bight, a branch passage joining the first arm between the stopper and the capillary to the second arm between the stopper and the bight, a valve in the branch passage, a reservoir for liquid branched off the second arm between the stopper and the bight, a collector in the second arm between the reservoir and the bight, a first bulb in the first arm above and adjacent the capillary, and a second bulb in the first arm above the first bulb, said viscometer further including a branch passage leading from the second arm and wherein the stopper for the second arm comprises a plug valve for closing the second arm below the branch passage.

* * * * *

UNITED STATES PATENT AND TRADEMARK OFFICE
CERTIFICATE OF CORRECTION

PATENT NO. : 4,583,395
DATED : April 22, 1986
INVENTOR(S) : Aylam V. Anantaraman It is certified that error appears in the above—identified patent and that said Letters Patent is hereby corrected as shown below:

The following lines are added on page 1 of the patent, between lines numbered [22] and [51] thereat:

--[30]   Foreign Application Priority Data

June 8, 1984   [CA]            Canada......................456144--

Signed and Sealed this

Sixteenth Day of September 1986

[SEAL]

Attest:

DONALD J. QUIGG

Attesting Officer    Commissioner of Patents and Trademarks